(12) United States Patent
Shkolnikov et al.

(10) Patent No.: US 11,801,509 B2
(45) Date of Patent: Oct. 31, 2023

(54) SERIAL CELLULAR ANALYTICS

(71) Applicant: Hewlett-Packard Development Company, L.P., Spring, TX (US)

(72) Inventors: Viktor Shkolnikov, Palo Alto, CA (US); Alexander Govyadinov, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 457 days.

(21) Appl. No.: 17/047,353

(22) PCT Filed: Aug. 10, 2018

(86) PCT No.: PCT/US2018/046205
§ 371 (c)(1),
(2) Date: Oct. 13, 2020

(87) PCT Pub. No.: WO2020/032970
PCT Pub. Date: Feb. 13, 2020

(65) Prior Publication Data
US 2021/0154672 A1     May 27, 2021

(51) Int. Cl.
*G01N 15/10*   (2006.01)
*B01L 3/00*    (2006.01)
*C12N 1/06*    (2006.01)

(52) U.S. Cl.
CPC ........ *B01L 3/502761* (2013.01); *C12N 1/066* (2013.01); *G01N 15/1031* (2013.01);
(Continued)

(58) Field of Classification Search
CPC ....... B01L 3/502761; B01L 2200/0652; B01L 2200/10; B01L 2300/0645; B01L 2300/0864; B01L 2400/0439; B01L 2400/0442; B01L 2300/087; B01L 2400/0487; B01L 2400/086; C12N 1/066;
(Continued)

(56) References Cited

U.S. PATENT DOCUMENTS 7,150,812 B2   12/2006   Huang et al.
9,309,559 B2    4/2016   Loudig et al.
(Continued)

FOREIGN PATENT DOCUMENTS

WO   WO-2014145152 A2   9/2014
WO   WO-2017184178      10/2017

OTHER PUBLICATIONS

Ahmad, Shazia et al. "Simultaneous extraction of nuclear and mitochondrial DNA from human blood", Genes Genet. Syst. (2007) 82, p. 429-432.

*Primary Examiner* — Alvaro E Fortich
(74) *Attorney, Agent, or Firm* — Foley & Lardner LLP (57) ABSTRACT

In one example in accordance with the present disclosure, a cellular analytic system is described. The cellular analytic system includes a series of analytic devices. Each analytic device includes 1) a separator to separate a cellular particle from a surrounding fluid, 2) an analyzer coupled to a first outlet of the separator to analyze the surrounding fluid, and 3) at least one lysing device coupled to at least a second outlet of the separator to rupture a membrane of the cellular particle. An outlet of the lysing device is fluidly coupled to a separator of a downstream analytic device.

15 Claims, 9 Drawing Sheets

(52) U.S. Cl.
CPC .. *G01N 15/1056* (2013.01); *B01L 2200/0652* (2013.01); *B01L 2200/10* (2013.01); *B01L 2300/0645* (2013.01); *B01L 2300/0864* (2013.01); *B01L 2400/0439* (2013.01); *B01L 2400/0442* (2013.01); *G01N 2015/1006* (2013.01); *G01N 2015/1081* (2013.01)

(58) Field of Classification Search
CPC ........... G01N 15/1031; G01N 15/1056; G01N 2015/1006; G01N 2015/1081; G01N 2015/0069; G01N 2015/1087; G01N 27/07; G01N 2001/4088; G01N 1/34; C12M 23/16; C12M 29/04
See application file for complete search history.

(56) References Cited

U.S. PATENT DOCUMENTS

| | | | |
|---|---|---|---|
| 9,895,694 B2 | 2/2018 | Kapur et al. | |
| 2002/0039783 A1* | 4/2002 | McMillan | C12M 47/06 435/259 |
| 2005/0250199 A1* | 11/2005 | Anderson | B01L 3/5027 435/288.5 |
| 2008/0023399 A1* | 1/2008 | Inglis | G01N 33/54366 210/209 |
| 2008/0193926 A1 | 8/2008 | Abraham-Fuchs et al. | |
| 2013/0210127 A1 | 8/2013 | Williams et al. | |
| 2015/0191717 A1 | 7/2015 | Santiago et al. | |
| 2016/0047735 A1* | 2/2016 | Grisham | G01N 15/1484 435/7.1 |
| 2017/0248508 A1 | 8/2017 | Ward et al. | |
| 2018/0008983 A1* | 1/2018 | McGuinness | B01L 3/502761 |

* cited by examiner

SERIAL CELLULAR ANALYTICS

BACKGROUND

Analytic chemistry is a field of chemistry that uses instruments to separate, identify, and quantify matter. In one particular example, cells and organelles within the cell can be extracted and analyzed. A wealth of information can be gleaned from the cells and from the surrounding fluid in which the cells are dispersed.

BRIEF DESCRIPTION OF THE DRAWINGS

The accompanying drawings illustrate various examples of the principles described herein and are part of the specification. The illustrated examples are given merely for illustration, and do not limit the scope of the claims.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

As described above, biochemistry involves the study and analysis of cellular components such as cells and organelles disposed within the cells. An analysis of the fluid that surrounds the cells and organelles can also be valuable for analytic purposes. For example, cytoplasmic fluid within the cell may provide a picture of the current mechanisms occurring within the cell. Examples of such mechanisms include ribonucleic acid (RNA) translation into proteins, RNA regulating translation, and RNA protein regulation, among others. As another example, nucleic fluid can provide a picture of potential mechanisms that may occur within a cell, mechanisms such as mutations. In yet another example, mitochondrial fluid can provide information as to the origin of the cell and the organism's matrilineal line.

While such fluids can provide valuable information for subsequent analysis, current methods of analyzing these fluids lack refinement and can inhibit the accuracy and reliability of their analysis. For example, such fluids may be analyzed together, or may be separated via enzymatic destruction of some components of the fluid. The mixing of the various fluids at an outset of an experiment is undesirable as without separating the different types of fluid, it is difficult to analyze them and isolate the above described information. For example, if cytoplasmic and nucleic fluid are mixed, it is difficult to discern which mechanisms are currently occurring (discovered through analysis of the cytoplasmic fluid) as compared to those mechanisms that could potentially occur (as discovered through analysis of the nucleic fluid). In other words, by analyzing mixed cellular fluids, valuable information may be lost.

Moreover, separation of the fluids may be complex and costly. For example, in analyzing each of the different fluids, i.e., extracellular, cytoplasmic, and nucleic, different samples may be used. That is multiple samples may be used, each for analyzing different fluids within the cellular structure. Accordingly, different samples and different analysis devices are implemented. Doing so is costly and ineffective.

As a specific example of biochemical analysis, extracellular fluid may be separated by centrifuging a sample and collecting the extracellular fluid. The cells are then gently lysed so as to rupture the cell membrane but to maintain the nuclear membrane intact. From the cell lysate, the nuclei are centrifuged out and the cytoplasmic fluid is collected. The nuclei and mitochondria are then separately lysed and an associated separated fluid is collected and analyzed. In other words, the complete analysis of a cell is performed in separate systems, or kits, from the system used for separation or concentration. This can result in complexity and the possibility of failure during, for example, transition from one system to another. This process is very laborious, and is also highly prone to contamination and operator error.

Accordingly, the present specification describes a system for separation and analysis of various sets of fluids including, but not limited to extracellular fluid, cytoplasmic fluid, nucleic fluid, and mitochondrial fluid. This is done via the sequential separation of different cellular components from the fluid in which they are dispersed and a selective and controlled on chip lysis operation. Specifically, the cellular analytic system includes an inlet, a first sorting subsystem to separate an extracellular fluid from a cell, and a first lysis system to lyse the cell membrane. The extracellular fluid is passed to an analyzer where it can be processed. The lysate from the cell is then passed to a second sorting subsystem, which separates organelles (such as nuclei and mitochondria) from the cytoplasmic fluid. The cytoplasmic fluid is passed to a second analyzer where it can be processed, and each of the organelles are passed to separate lysing devices where they can be lysed. Additional sorting and lysing devices can be appended to separate and lyse further divisions of the organelles. As described herein, such a system simultaneously and automatically provides information on the cells environment (from the extracellular fluid), the mechanisms actively occurring at the cell (from the cytoplasmic fluid), the mechanisms that have the potential to occur (from the nucleic fluid), and about the organisms lineage (from the mitochondrial fluid).

Specifically, the present specification describes a cellular analytic system. The cellular analytic system includes a series of analytic devices. Each analytic device includes 1) a separator to separate a cellular particle from a surrounding fluid, 2) an analyzer coupled to a first outlet of the separator to analyze the surrounding fluid, and 3) at least one lysing device coupled to at least a second outlet of the separator to rupture a membrane of the cellular particle. In this example, an outlet of a lysing device is fluidly coupled to a separator of a downstream cellular preparation device.

The present specification also describes a method. In a first analytic device, a cellular particle is separated from a surrounding fluid. The surrounding fluid is passed to an analyzer chamber and analyzed. The cellular particle is passed to a lysing device and a membrane of the cellular particle is ruptured. A lysate of the ruptured cellular particle is passed to a second analytic device.

In another example of a cellular analytic system, a first analytic device includes a first separator to separate a cell from an extracellular fluid. A first analyzer of the first analytic device is coupled to a first outlet of the first separator to analyze the extracellular fluid. A first monitored lysing device is coupled to a second outlet of the first separator to rupture a membrane of the cell. The cellular analytic system also includes a second analytic device. The second analytic device includes a second separator to separate organelles in the lysate of the cell from a cytoplasmic fluid. A second analyzer of the second analytic device is coupled to a first outlet of the second separator to analyze the cytoplasmic fluid. A second monitored lysing device is coupled to a second outlet of the second separator to rupture a membrane of a first organelle.

As used in the present specification and in the appended claims, the term "cellular particle" refers to various components of a cell as well as the cell itself. For example, a cellular particle refers to a cell, a nuclei within the cell, mitochondria within the cell, and other particles.

Further, as used in the present specification and in the appended claims, the term "cell membrane" refers to any enclosing structure of a cell, organelle, or other cellular particle.

In summary, using such a cellular analytic system 1) automates the sequential analysis of different fluids within a sample; 2) enlarges the information collectable from a sample; 3) avoids contamination of fluid samples; and 4) reduces the number of samples used in multi-fluid analysis. However, the devices disclosed herein may address other matters and deficiencies in a number of technical areas.

Figure 1:
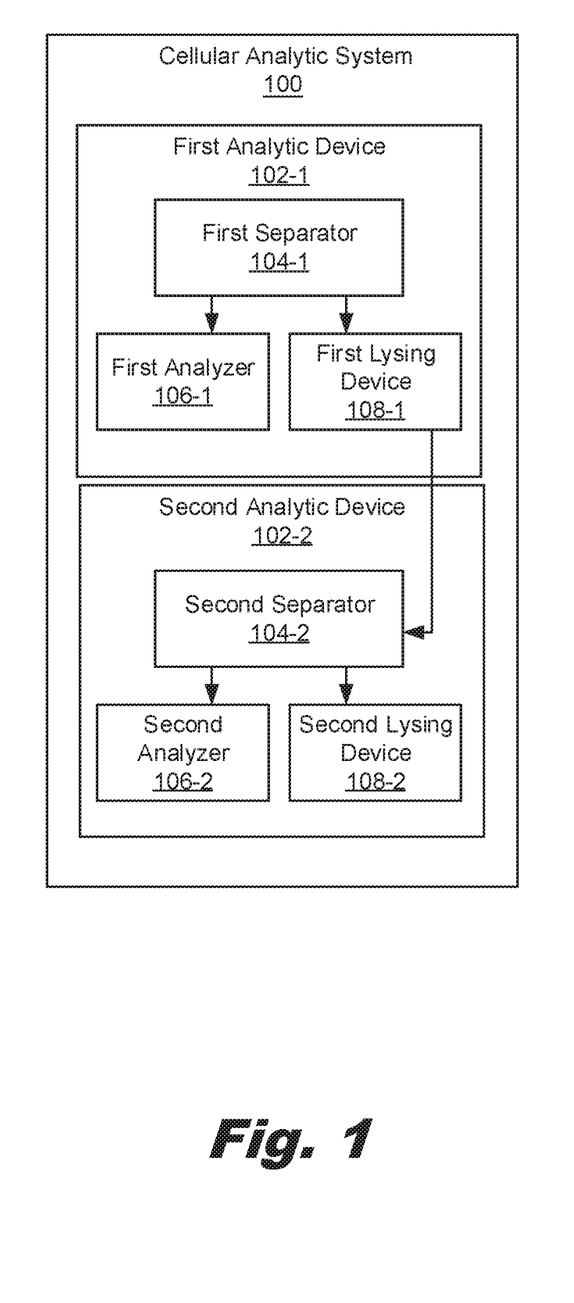
FIG. 1 is a block diagram of a serial cellular analytic system, according to an example of the principles described herein.

Turning now to the figures, FIG. 1 is a block diagram of a serial cellular analytic system (100), according to an example of the principles described herein. As described herein, the cellular analytic system (100) is a collection of components for separating and analyzing a fluid sample. In some examples, the cellular analytic system (100) is part of a lab-on-a-chip device. A lab-on-a-chip device combines several laboratory functions on a single integrated circuit which may be disposed on a silicon wafer. Such lab-on-a-chip devices may be a few millimeters to a few square centimeters, and provide efficient small scale fluid analysis functionality.

In other words, the components, i.e., the separators (104), analyzers (106), and lysing devices (108) may be microfluidic structures. A microfluidic structure is a structure of sufficiently small size (e.g., of nanometer sized scale, micrometer sized scale, millimeter sized scale, etc.) to facilitate conveyance of small volumes of fluid (e.g., picoliter scale, nanoliter scale, microliter scale, milliliter scale, etc.).

The cellular analytic system (100) includes a series of analytic devices (102) each which process a cellular particle at a particular stage. For example, a first analytic device (102-1) may receive as an input, a fluid sample and may output a lysate of the cell, which may be nuclei, mitochondria, and other organelles dispersed in a cytoplasmic fluid.

The second analytic device (102-2) may receive as an input the output of the first analytic device (102-1). As a specific example, the output lysate from the first lysing device (108-1) is received in the separator (104-2) of the second analytic device (102-2). The second analytic device (102-2) may pass a lysate of the nuclei and mitochondria to a subsequent analytic device (102). While specific reference is made to two analytic devices (102-1, 102-2) that operate on specifically referenced cellular particles, the present cellular analytic system (100) may include any number of analytic devices (102-1, 102-2) that operate on any variety of cellular particles.

Figure 2:
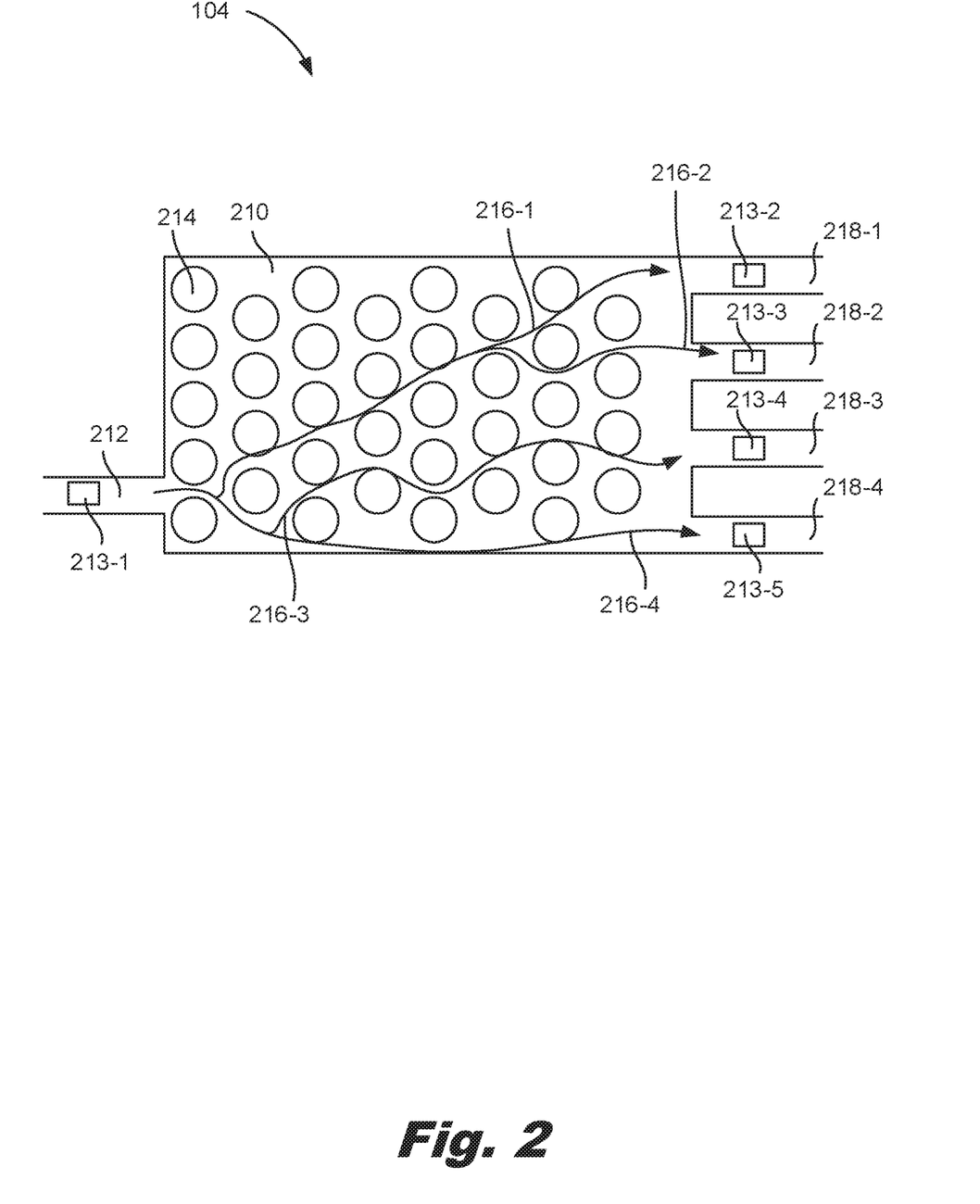
FIG. 2 is a diagram of a separator of the serial cellular analytic system, according to an example of the principles described herein.

Each analytic device (102-1, 102-2) includes a separator (104) to separate a cellular particle from a surrounding fluid. The cellular particle and surrounding fluid may be distinct per separator (104-1, 104-2). For example, the first separator (104-1) may separate cells from an extracellular fluid in which they are dispersed and the second separator (104-2) may separate nuclei and mitochondria from the cytoplasmic fluid in which they are dispersed. The separator(s) (104) may use a variety of mechanisms to separate the cellular particles from their surrounding fluid. For example, the separator (104) may include a separation chamber having an array of posts or columns that are arranged to facilitate separation of particles in the flow based on the size of the particles. That is, as the sample passes through the separators (104-1, 104-2), the particles therein strike the posts. Particles of different sizes generally follow different flow paths such that the particles can be separated from the fluid in which they are dispersed. FIG. 2 below provides an example of such a separator (104).

In another example, the separator (104) is a dielectrophoresis separator (104). In this example, electrodes within a chamber includes a signal generator that produces a non-uniform electrical field. The non-uniformity of the field directs particles of different sizes in different directions. For example, particles of one size may flow up a gradient of the non-uniform field and particles of another size may flow down the gradient of the non-uniform field. According to this operation, the dielectrophoresis separator (104) can separate different components within a surrounding fluid.

Each analytic device (102) also includes an analyzer (106) to analyze the surrounding fluid. As the surrounding fluid received by each analyzer (106) may be different, the analyzer (106) in each analytic device (102) may be different. For example, the first analyzer (106-1) may be set to analyze an extracellular fluid while the second analyzer (106-2) may be set to analyze a cytoplasmic fluid.

The analyzers (106) receive a fluid and analyze it. For example, the analyzers (106) may include detection components to identify characteristics of the biological material. For example, the analyzers (106) may include a hybridization detection component and a bacterial fluid detection component. The hybridization detection component may detect characteristics of the fluid such as electrochemical properties or fluorescence.

In a example, an analyzer (106) may include a microarray for antigens that include proteins, nucleic acids, sugars, and other small molecules. In yet another example, an analyzer (106) may include a pH sensor which sensor may be a membrane sensitive to pH. Such a sensor may determine a carbon dioxide concentration which is indicative of cellular metabolism. Other examples of operations that may be carried out by the analyzer (106) include different forms of nucleic acid testing such as nucleic acid amplification such as polymerase chain reaction operations, or isothermal nucleic acid methods such as loop-mediated isothermal amplification (LAMP) and recombinase polymerase amplification (RPA), among others.

Each analytic device (102) also includes a lysing device (108) that receives a cellular particle as separated from its surrounding fluid. For example, the first lysing device (108) may receive a cell as it is separated from the extracellular fluid and the second lysing device (108) may receive different organelles such as nuclei and mitochondria as they are separated from the cytoplasmic fluid.

Lysis is a process of extracting cellular components for purposes such as purifying the components, retrieving DNA and RNA proteins, polypeptides, metabolites, and small molecules or other components therein, and analyzing the components for genetic and/or disease characteristics. Lysis ruptures a cellular particle membrane and frees the inner components. The fluid containing the inner components is referred to as lysate. The contents of the cellular particle can then be analyzed by a downstream system. Lysis can be executed using any number of method, including shearing, ball milling, pestle grinding, and using rotating blades to grind the membranes. Other examples of lysis include localized heating and shearing by constriction. In another example, repeated cycles of freezing and thawing can disrupt cells through ice crystal formation. Solution-based lysis is another example wherein contents of a cellular particle are extracted. In these examples, the osmotic pressure in the cellular particle could be increased or decreased to collapse the cell membrane or to cause the membrane to burst.

In one example, lysis is triggered via a thermal resistor disposed within a microfluidic channel. The thermal resistor generates a vapor bubble. The expansion and collapse of the vapor bubble both produce a high pressure spike within the channel. This high pressure spike and the high shear within this localized area lyses a cellular particle within the localized area. In a particular example, a method of cell lysis includes moving a sample through a microfluidic channel. A lysing element in the microfluidic channel is activated to lyse the cellular particle. Lysate fluid resulting from the activation of the lysing element is then moved through the microfluidic channel. While particular examples of cell lysis mechanisms have been described herein, a variety of cell lysis mechanisms are used in biochemical analytics.

As described above, the output of the lysing device (108) is passed to a downstream analytic device (102) and in particular to a downstream separator (104). Thus, a sequence of separation and analysis is performed. The present cellular analytic system (100) capitalizes on the fact that the different cellular fluids are initially separated, i.e., extracellular is separated from the cytoplasmic via a cell membrane. Rather than mixing them during analytics, the cellular analytic system (100) maintains them separate such that the information that can be collected from each fluidic analysis is isolated and uncontaminated via other types of cellular fluid. Moreover, the system (100) by being entirely contained, prevents contamination at any stage of the analytic process.

FIG. 2 is a diagram of a separator (104) of the serial cellular analytic system (FIG. 1, 100), according to an example of the principles described herein. As described above, the separator (104) in some examples includes an array of columns (214) spaced apart to facilitate separation of cellular particles form the surrounding fluid based on a size of the cellular particles. While FIG. 2 depicts a particular type of separator (104), other types of separators (104) may be used to separate cellular particles form the surrounding fluid in which they are dispersed.

In this particular example, cellular particles are sorted by directing the sample, which includes the cellular particles, through an input channel (212) and into a separation chamber (210). The separation chamber (210) includes an array of columns (214), or posts that are spaced apart so as to direct cellular particles in the sample along different flow paths based on the size of the particles.

In some examples, the columns (214) may be arranged in a particular arrangement, such as one that coincides with deterministic lateral displacement (DLD). DLD uses a specific arrangement of obstacles such as the columns (214) to control the path of particles to separate particles larger than a threshold diameter from those smaller than the threshold diameter through collisions with the obstacles. That is, in a flow, when a particle is larger than the threshold diameter, its center is positioned such that collision with an obstacle causes the larger particle to flow to one side of the obstacle, while collision of objects smaller than the threshold diameter with the same obstacle causing the smaller particles to flow to the other side of the obstacle. Accordingly, particles of different sizes are directed to different output channels (218).

While FIG. 2 depicts the columns (214) as having a particular shape and size, the columns (214) may be formed having any cross-sectional shape and size. Moreover, while FIG. 2 depicts the columns (214) in a particular configuration, the columns (214) may be arranged in any configuration.

To generate the flow to drive a sample through the separator (104), the separator (104) may include an inlet pump (213-1) disposed within the input channel (212). In some examples, the inlet pump (213-1) may be an integrated pump. In some examples, the inlet pump (213-1) may be an inertial pump which refers to a pump which is in an asymmetric position within the inlet. The asymmetric positioning within the inlet facilitates an asymmetric response of the fluid to the pump (213-1). The asymmetric response results in fluid displacement when the pump (213-1) is actuated. In some examples, these inlet pumps (213-1) may be thermal inkjet resistors, or piezo-drive membranes or by any other displacement device. To more completely draw a sampled through the separator (104), the separator (104) may include pumps (213-2, 213-3, 213-4, 213-5) disposed in outlets. Similarly, the outlet pumps (213-2, 213-3, 213-4, 213-5) may be thermal inkjet resistors, or piezo-drive membranes or by any other displacement device.

In some examples, the cellular particles in the sample may include different categories of particles. For example, the sample may include solid particles, soft particles, gas bubbles, biological cells, bacteria, and/or droplets of fluid. In another example, the different categories may be different types of cells. For example, the cells may be blood cells, mammalian cells, plant cells, or other types of cells. Returning to the separation chamber (210), the columns (214) cause the cellular particles to separate according to size. Accordingly, the separation chamber (210) may include different output channels (218-1, 218-2, 218-3, 218-4), each in fluid communication with different downstream devices and positioned to receive particles of a certain category, size, or range of sizes. Specifically, one of the output channels (218) may be positioned to receive cell-sized particles.

While FIG. 2 depicts the separation of the particles within the sample into four different flow paths (216-1, 216-2, 216-3, 216-4), any number of flow paths may be established based on the configuration of the columns (214) within the separation chamber (210).

As depicted in FIG. 2, a separation chamber (210) may have multiple outlets (218). In this example, each of the different outlets (218) may be coupled to a different lysing device (FIG. 1, 108). For example, a first outlet (218-1) may receive one type or size of cell and a second outlet (218-2) may receive a different type, or different size cell. Each of these outlets (218) may be coupled to distinct lysing devices (FIG. 1, 108) that rupture cellular particle membranes or walls and pass them along for subsequent operations. As described above, each of these distinct lysing devices (FIG. 1, 108) may be coupled to downstream analytic devices (FIG. 1, 102). Accordingly, a tree of analytic devices (FIG. 1, 102) can be implemented.

Figure 3:
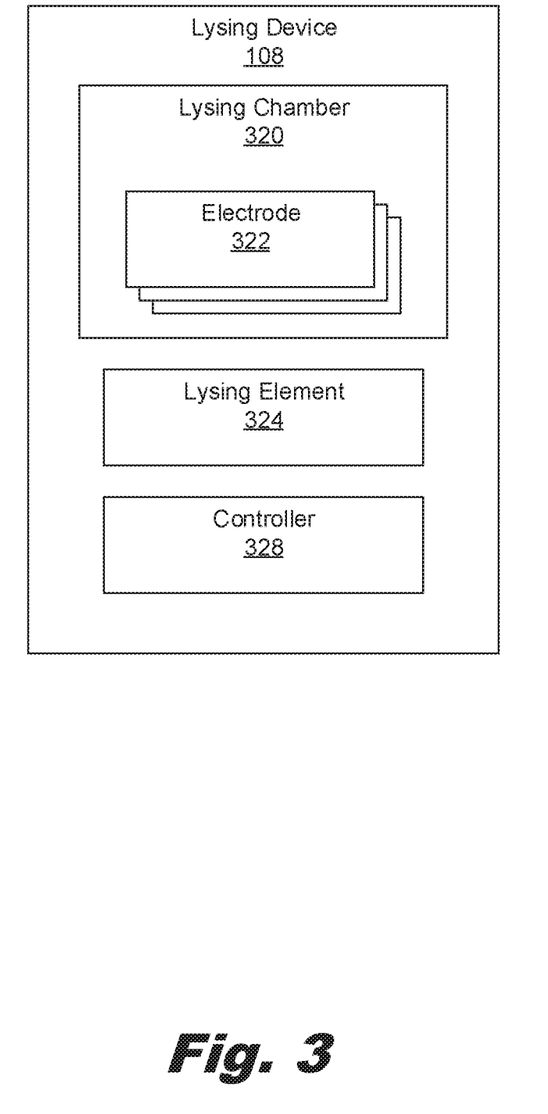
FIG. 3 is a block diagram of a lysis device of the serial cellular analytic system, according to an example of the principles described herein.

FIG. 3 is a block diagram of a lysing device (108), according to an example of the principles described herein. As cell lysis is an operation in many sample preparation protocols for the characterization of nucleic acid or protein contents of a cell, the quality of cell lysis can have a direct impact on downstream operations. For example, if the lysis has poor efficiency, the amount of material to be analyzed may be reduced. Poor lysis can also affect the analytic results as those cells that are not lysed are excluded from the analysis. On the other hand, if the lysis conditions are too harsh, the nucleic acid and/or protein material may deteriorate. Doing so similarly degrades the information that can be obtained from the sample.

Accordingly, in some examples, the lysing device (108) may be a monitored lysing device (108) meaning that the lysis operation that occurs therein is monitored to ensure lysis occurs as desired. That is, the monitored lysing device (108) provides a quality control check over a lysing operation. Specifically, the lysing device (108) includes a lysing chamber (320) where lysing occurs. In some examples, the lysing chamber (320) may be no more than 100 times a volume of a cellular particle to be lysed. In other examples, the lysing chamber (320) may be of a size comparable with the cellular particle and in some cases even smaller so as to deform the cellular particle before or during the rupturing of the membrane. That is, the lysing chamber (320) may be a microfluidic structure. As the lysing chamber (320) is the location where lysis occurs, the lysing chamber (320) receives, through an input, a cellular particle or other component to be lysed.

In some examples as will be described below, the lysing chamber (320) may have a reduced cross-section relative to inlets and outlets. The reduced cross-section of the lysing chamber (320) creates a constriction, which acts as a lysing element in some examples. That is, the reduced cross-section of the lysing chamber (320) increases pressure within the fluid, which can cause the cellular particle membrane/wall to rupture.

The lysing device (108) also includes a lysing element (324) to rupture a membrane. That is, a cell and/or organelle has a wall or a membrane. In some examples, the lysing element (324) is disposed outside of the lysing chamber (320) and in others, the lysing element (324) is disposed within the lysing chamber (320).

The lysing element (324) may take many forms. For example, lysing may occur simply by pushing the cells through a constriction. In this example, the lysing element (324) may be a transition between a wide input to a narrower lysing chamber (320). In other examples, the lysing element (324) may be a physical element. For example, the lysing element (324) may be a thermal inkjet resistor. That is, the lysing element (324) may include a firing resistor. The firing resistor heats up in response to an applied current. As the firing resistor heats up, a portion of the fluid in the lysing chamber (320) vaporizes to generate a bubble. This bubble generates a pressure and shear spike which ruptures the cellular particle membrane. In this example, the lysing element (324) may be a thermal inkjet (TIJ) lysing element (324). As used in the present specification and in the appended claims, a thermal inkjet lysing element (324) refers to a lysing element that uses elements similar to a TIJ element on a printer, but that does not implement ink.

In another example, the lysing element (324) may be a piezoelectric device. As a voltage is applied, the piezoelectric device changes shape which generates a pressure pulse in the lysing chamber (122) that creates the shear which ruptures the cellular particle membrane. In this example, the lysing element (324) may be a piezoelectric inkjet (PIJ) lysing element (324). As used in the present specification and in the appended claims, a piezoelectric inkjet lysing element (324) refers to a lysing element that uses elements similar to a PIJ element on a printer, but that does not implement ink.

In yet another example, the lysing element (324) may be an electrostatic membrane or other mechanical actuator. While particular reference is made to particular lysing elements (324), any number of lysing elements (324) could be used in accordance with the principles described herein, a few examples of which have been provided above.

The lysing device (108) also includes at least one pair of electrodes (322) disposed within the lysing chamber (320). These electrodes (322) detect a level of conductivity within the lysing chamber (320). That is, incoming cellular particles to a lysing chamber (320), and the solution in which they are contained, have a predetermined electrical conductivity. Any change to the contents of the lysing chamber (320) will effectively change the electrical conductivity within the lysing chamber (320). Specifically, as the particle walls or membranes are ruptured and the lysate pours out, the conductivity may increase. To measure the conductivity, a resistance of solution between electrode (322) plates is measured and a conductivity determined therefrom. In some examples, a single pair of electrodes (322) are used, with one electrode plate placed at either end of a lysing chamber (320). In another example, multiple pair of electrodes (322) are used. For example, one pair of electrode (322) plates could be placed at the inlet and another pair of electrode (322) plates placed at the outlet. In other examples, a three electrode (322) or a four electrode (322) system could be used.

The lysing device (108) also includes a controller (328) to determine when the cellular particle membrane has ruptured based on detected levels of conductivity in the lysing chamber (320). That is, the controller (328) may compare detected levels of conductivity within the lysing chamber (320) with a threshold level of conductivity associated with a ruptured cell. Accordingly, once the detected level of conductivity within the lysing chamber (320) has reached the threshold value, the controller (328) may determine that a cell has been ruptured.

The controller (328) may additionally include electronics (not shown) for communicating with and controlling the various components of lysing device (108). As a specific example, the controller (328) may control operation of the pumps used during lysis. For example, if the electrode (322) output indicates that a cellular particle has not ruptured or is otherwise not sufficiently lysed, the controller (328) may activate various combinations of pumps to return the cellular particle to the lysing chamber (320) such that a second attempt at lysing can be carried out. As described above such an operation may be used to monitor the lysing of different types of cellular particles including cells, nuclei, and mitochondria among others.

To determine whether a cellular particle has been lysed, the controller (328) may receive the measurements of the electrodes (322). That is, the electrodes (322) may provide a conductivity measurement. The controller (328) can compare this value to a threshold conductivity value that maps to a desired level of lysis. If the measured value is greater than the reference value, a determination made, and a count incremented, regarding cell lysis. By comparison, if the measured value is less than the reference value, the controller (328) may activate certain components to re-deploy the lysing element (324) in a second attempt to lyse the particular cellular particle. Thus a controlled feedback for lysis is achieved based on monitoring the conductivity within a lysing chamber (320) where the lysing occurs.

Such control can provide a closed-loop feedback to ensure complete lysis. Moreover, such control can be used to control lysing parameters such as lysing intensity and lysis duration. The lysing device (108) having more control therein, enhances the efficiency of downstream analytics as subsequent systems can know with certainty an amount of starting material. Such knowledge increases the reliability and credibility of any final results/analysis.

Figure 4:
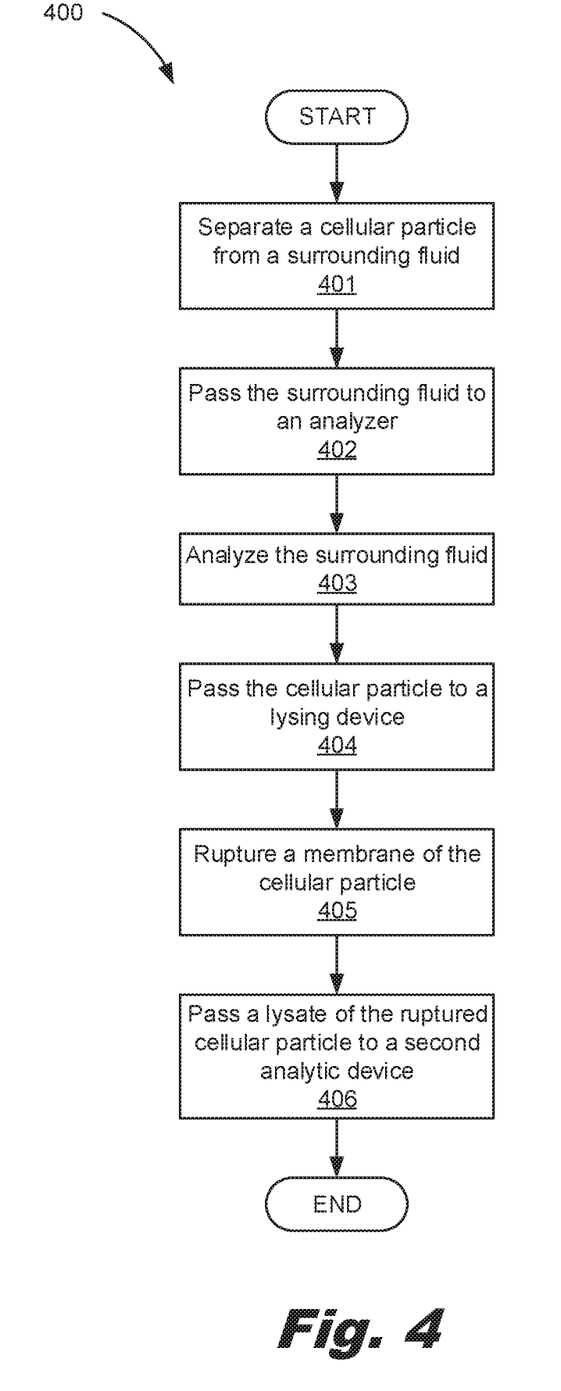
FIG. 4 is a flowchart of a method for serial separation and lysis in a serial cellular analytic system, according to an example of the principles described herein.

FIG. 4 is a flowchart of a method (400) for serial separation and lysis in a cellular analytic system (FIG. 1, 100), according to an example of the principles described herein. As described, the cellular analytic system (FIG. 1, 100) allows for sequential separation of particular cellular particles from their surrounding fluid. That is, in a first analytic device (FIG. 1, 102-1), a first cellular particle is separated from its surrounding fluid. The separated particle is lysed and the lysate passed to a second analytic device (FIG. 1, 102-2) where the lysate is further separated. Thus, a cascade of separation, analysis, and lysing operations are proscribed wherein different fluids can be analyzed separately from one another, thus improving the data that can be collected based on the characteristics of that fluid.

Specifically, in a first analytic device (FIG. 1, 102), a cellular particle is separated (block 401) from a surrounding fluid. As described above, this separation may occur in a number of ways. In one particular example, a separator (FIG. 1, 104) includes a separation chamber (FIG. 2, 210) with an array of columns (FIG. 2, 214). A flow is generated through the separation chamber (FIG. 2, 210) and as particles strike the columns (FIG. 2, 214) particles of different sizes flow along different flow paths (FIG. 2, 216). In other words, cellular particles of a particular size flow along a same path while the surrounding fluid travels along a different flow path. That is, the surrounding fluid is passed along one path and the cellular particles along another.

The surrounding fluid is passed (block 402) to an analyzer (FIG. 1, 106) where it can be analyzed (block 403) based on the type of fluid. That is, depending on whether the surrounding fluid is an extracellular fluid, a cytoplasmic fluid, a nucleic fluid, a mitochondrial fluid or some other type of fluid, particular analytic operations can be executed. Examples of such operations include amplification, polymerase chain reaction, or other forms of nucleic acid testing.

By comparison, the cellular particle of interest is passed to another outlet. Specifically, the cellular particle may be passed (block 404) to an outlet (FIG. 2, 218) that leads to a lysing device (FIG. 1, 108). That is, the array of columns (FIG. 2, 214) can be selected such that the flow path of cellular particles of a particular type, i.e., size, can be determined. An outlet (FIG. 2, 218) through which a cellular particle flow path passes may be coupled to a lysing chamber (FIG. 3, 320) of a lysing device (FIG. 1, 108).

Within the lysing chamber (FIG. 3, 320), the particular cellular particle may be lysed. That is, the membrane of the cellular particle may be ruptured (block 405). The characteristics of the lysing operation may depend upon the type of cellular particle that is to be lysed. For example, a gentler lysing may be executed to rupture a cellular membrane so as to not also lyse the nuclear membrane disposed within a cell. Accordingly, the series of lysing devices (FIG. 1, 108) may include different lysing elements (FIG. 3, 322) or lysing elements (FIG. 3, 322) having different lysing parameters.

The lysate of the ruptured cellular particle is then passed (block 406) to a second analytic device (FIG. 1, 102-2). For example, once a cell has been lysed, the lysate, e.g., the nuclei and mitochondria in a cytoplasmic fluid, is passed to a second analytic device (FIG. 1, 102-2) where 1) it can be further separated, 2) the cytoplasmic fluid can be analyzed, and 3) the nuclei and mitochondria can be lysed. Thus, the method (400) provides a way of separating the analysis of the first surrounding fluid, for example in the first analyzer (FIG. 1, 106-1) and the second surrounding fluid, for example in the second analyzer (FIG. 1, 106-2). Thus, more data can be collected from each of these. That is, if such fluids were mixed when performing the analysis, the data gleaned therefrom would be obfuscated. Moreover, the sequential separation and lysing allows a single sample to provide different types of fluid for analysis, rather than requiring a single sample per type of fluid to be analyzed.

Figure 5:
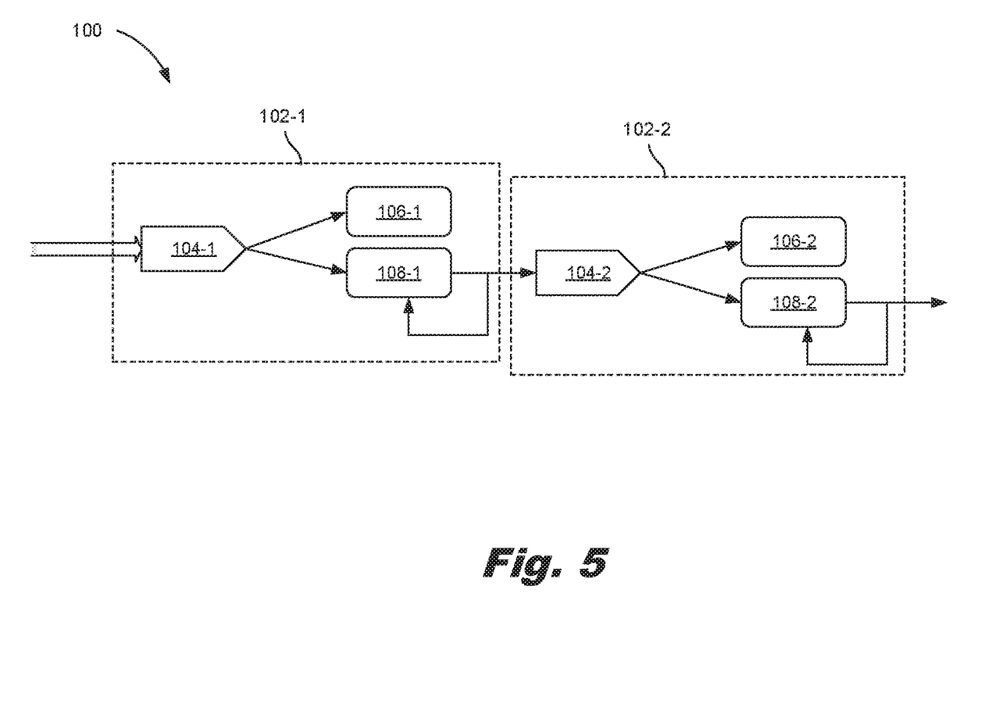
FIG. 5 is a diagram of a serial cellular analytic system, according to an example of the principles described herein.

FIG. 5 is a diagram of a serial cellular analytic system (100), according to an example of the principles described herein. As described above, the present specification describes the sequential analysis of different fluids found within a fluidic sample. Accordingly, a sample is received in a first analytic device (102). Specifically, the sample is received at a first separator (104-1) of the first analytic device (102-1). The sample may be of varying types. For example, the sample may include cells cultured from plants, animals, or bacteria which cells are suspended in an appropriate extracellular fluid medium such as interstitial fluid and blood plasma. For example, the cell fluid may include whole blood or components of blood including plasma in which red and white blood cells are suspended.

As described above, the separators (104) operate to separate a cellular particle from the surrounding fluid. For example, in a first analytic device (102-1), the first separator (104-1) separates a cell from the extracellular fluid in which it is dispersed. The extracellular fluid is passed to a first analyzer (106-1) which is coupled to a particular outlet (FIG. 2, 218) which corresponds to the flow path of the extracellular fluid. In the first analyzer (106-1), an analysis can be carried out on the extracellular fluid to collect information therefrom. For example, an analysis of the extracellular fluid may indicate information on the environment of the cell. Note that such analysis is contaminant free. That is the extracellular fluid is not mixed with other fluids such as cytoplasmic fluid. The presence of additional fluids may obfuscate the results of an analysis of the extracellular fluid.

Figure 6:
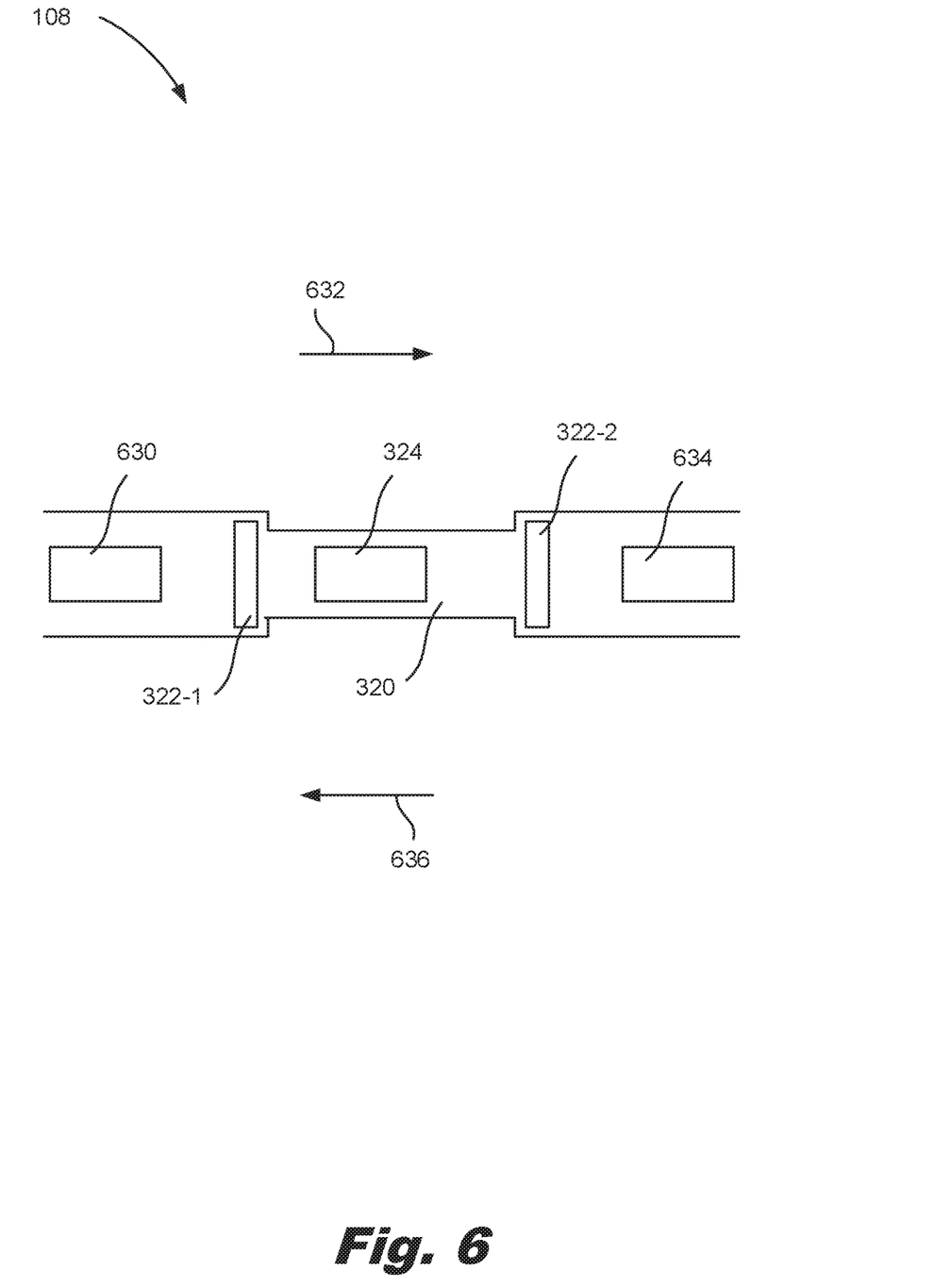
FIG. 6 is a diagram of a monitored lysis device of the serial cellular analytic system, according to an example of the principles described herein.
Figure 7:
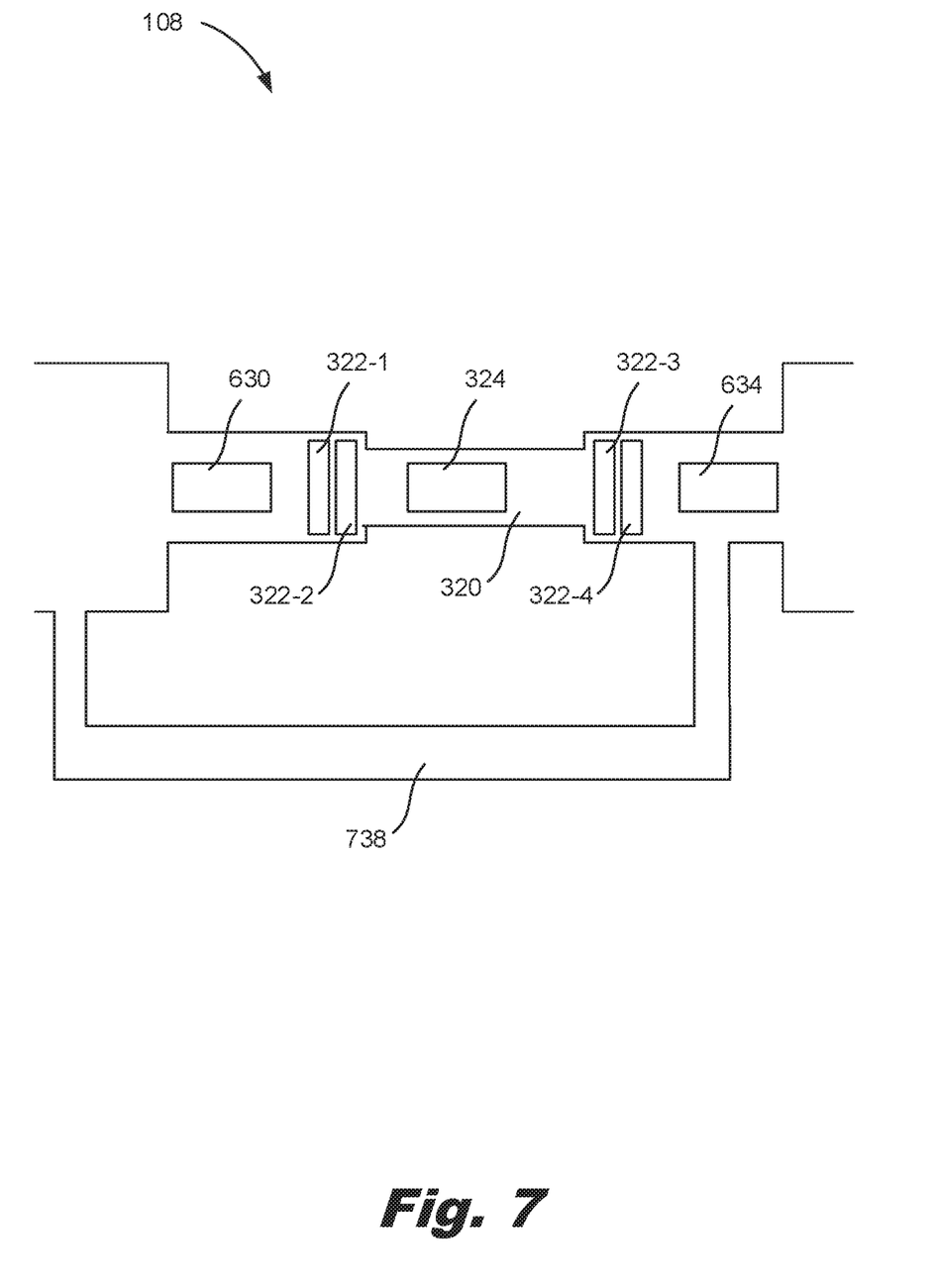
FIG. 7 is a diagram of a monitored lysis device of the serial cellular analytic system, according to another example of the principles described herein.

The cell, by comparison is directed via the array of columns (FIG. 2, 214) in the separation chamber (FIG. 2, 210) towards another outlet (FIG. 2, 218) that leads to a first lysing device (108-1), which may be a monitored lysing device (108-1). That is, a feedback loop may be implemented as described above to ensure that the cell membrane is sufficiently ruptured such that the lysate therein is expelled. FIGS. 6 and 7 provide examples of the re-lysing that can occur during such monitored lysing.

When the cell has been lysed to a satisfactory degree, the lysate of the cells, that is the organelles such as mitochondria, bacteria, and nuclei are passed to a second analytic device (102-2) and specifically to a second separator (104-2) that is found in the second analytic device (102-2).

Similar to the first separator (104-1), the second separator (104-2) separates the organelles in the lysate from the surrounding fluid, which surrounding fluid is a cytoplasmic fluid. The cytoplasmic fluid via the action of the second separator (104-2) is passed to a second analyzer (106-2) where it can be analyzed using either the same or different analysis mechanisms as the first analyzer (106-1). For example, an analysis of the cytoplasmic fluid may indicate mechanisms that are occurring at the cell at the time of lysis. Note that such analysis is contaminant free. That is the cytoplasmic fluid is not mixed with other fluids such as extracellular fluid. The additional fluids may obfuscate the results of an analysis of the extracellular fluid, thus analysis of a clean cytoplasmic fluid increases the accuracy of any analysis.

The organelles, by comparison are directed via the array of columns (FIG. 2, 214) in the separation chamber (FIG. 2, 210) towards another outlet (FIG. 2, 218) that leads to a second lysing device (108-2), which may be a monitored lysing device (108-2). That is, a feedback loop may be implemented as described above to ensure that the organelle membrane is sufficiently ruptured such that the lysate therein is expelled.

When the organelle has been lysed to a satisfactory degree, the lysate of the organelles can be passed to a downstream analytic device (102) where subsequent analysis can be effectuated. As can be seen, any number of analytic devices (102) may be cascaded such that any number of separation and analysis operations are carried out. Thus, a wide variety of options regarding cellular analysis are provided by the cellular analytic system (100) of the present specification.

FIG. 6 is a diagram of a monitored lysing device (108), according to an example of the principles described herein. FIG. 6 clearly depicts the lysing chamber (320) to receive the cellular particle to be lysed. In some examples, such as that depicted in FIG. 6, the lysing chamber (320) has a reduced cross-section relative to the inlet and a reduced cross-section relative to the outlet. The reduced cross-section of the lysing chamber (320) creates a constriction, which acts as a lysing element in some examples. That is, the reduced cross-section of the lysing chamber (320) increases pressure within the fluid, which can cause the cellular particle membrane/wall to rupture.

As described above, the lysing device (108) also includes a lysing element (324). As described above, in some examples the lysing element (324) may reside within the lysing chamber (320). In other examples, the lysing element (324) may reside outside of the lysing chamber (320) yet produce a lysing effect within the lysing chamber (320). For example, the lysing element (324) may be an ultrasonic device that generates high energy sonic waves. These high energy waves may travel through the wall of the lysing chamber (320) to shear the cells disposed therein.

While particular reference is made to a particular lysing element (324) other lysing elements (324), some of which have been described above, may be implemented in accordance with the principles described herein.

FIG. 6 also clearly depicts the pair of electrodes (322-1, 322-2) that are disposed in the lysing chamber (320). As described above, these electrodes (322) may be metallic plates with a gap between them that can detect a resistance of a fluid in the gap. The measured resistance is indicative of a conductivity of the solution in the lysing chamber (320). In this example, the lysing device (108) includes a single pair of electrodes (322-1, 322-2), with a plate disposed on either side of the lysing chamber (320). In this example, a single value is measured which is indicative of a conductivity within the entirety of the lysing chamber (320).

As described above, in some examples a flow is generated through the lysing chamber (320). To generate such a flow, the lysing device (108) includes a main pump (630). That is, the main pump (630) directs fluid from the inlet through the lysing chamber (320) and past the lysing element (324) and electrodes (322). The main pump (630) may take many forms. For example, the main pump (630) may be integrated into a wall of the lysing chamber (320). More specifically, the main pump (630) may be a thermal resistor that is integrated into a wall of the lysing chamber (320). As used in the present specification, a wall refers to any wall of the chamber and may include a sidewall, a ceiling, and/or a floor.

In some examples, the main pump (630) is a TIJ pump. That is, as a firing resistor heats up, a portion of the fluid in the inlet vaporizes to generate a bubble. This bubble pushes fluid through the inlet into the lysing chamber (320). In this example, the main pump (630) may be a TIJ pump.

In another example, the main pump (630) may be a piezoelectric device. As a voltage is applied, the piezoelectric device changes shape which generates a pressure pulse that pushes the fluid into the lysing chamber (320). In this example, the main pump (630) may be a PIJ pump. In yet another example, the main pump (630) may be an electrostatic membrane.

In some examples, the lysing device (108) also includes a return pump (634) which can re-direct fluid flow back to the lysing chamber (320). As with the main pump (630), the return pump (634), may be a TIJ pump, a PIJ pump, an electrostatic membrane or other mechanical actuator.

The main pump (630), upon activation may direct a cellular particle through the lysing chamber (320) as indicated by the arrow (632), that is, past the lysing element (324). When a sensed conductivity indicates that the cellular particle has not ruptured, the controller (FIG. 3, 328) may operate to return the cellular particle to the lysing chamber (320) for a second attempt. In this example, the controller (FIG. 3, 328) de-activates the main pump (630) so as to stop the flow in the direction indicated by the arrow (632). The controller (FIG. 3, 328) then activates the return pump (634) such that a flow is generated in the direction indicated by the arrow (636) such that the cellular particle may be re-lysed. That is, the return pump (634) re-directs the cellular particle to the lysing chamber (320) through an outlet of the lysing chamber (320). In some examples, such a feedback operation may be performed automatically such that a closed loop feedback may be exhibited without user involvement.

FIG. 7 is a diagram of a monitored lysing device (108), according to another example of the principles described herein. In this example, rather than having a single pair of electrodes (322), the lysing chamber (320) includes multiple pairs of electrodes (322). Specifically, a first pair of electrodes (322-1, 322-2) may be disposed near an inlet of the lysing chamber (320) and a second pair of electrodes (322-3, 322-4) may be disposed near an outlet of the lysing chamber (320). In this example, each pair of electrodes (322) may determine a conductivity between the corresponding plates and a difference used to determine lysing and/or cell presence. That is, a first pair of electrodes (322-1, 322-2) determine a conductivity at an inlet and a second pair of electrodes (322-3, 322-4) determine a conductivity at an outlet. The results can be compared and if a difference between the two is greater than a threshold amount, it may be determined that a cellular particle is present and/or whether that cellular particle has been sufficiently lysed.

In the example depicted in FIG. 7, the lysing device (108) further includes a return channel (738) through which the return pump (634) re-directs fluid to the lysing chamber (320). That is, rather than re-directing an un-lysed cellular particle against the flow generated by the main pump (630), fluid is directed through the return channel (738). In this example, the main pump (630) is not de-activated when an un-lysed cellular particle is detected. Rather, it is maintained active to help draw fluid through the return channel (738) to the lysing chamber (320). Note that while FIG. 7 depicts multiple pairs of electrodes (322) used with a return channel (738), in some examples, a single pair of electrodes (322) as described in FIG. 6 may be used in an example with a return channel (738). Moreover, while FIG. 6 depicts a single pair of electrodes (322) in an example where fluid is re-directed through the outlet, in some examples, multiple pairs of electrodes (322) as described in FIG. 7 may be used in the example with the flow that is re-directed through the outlet.

Figure 8:
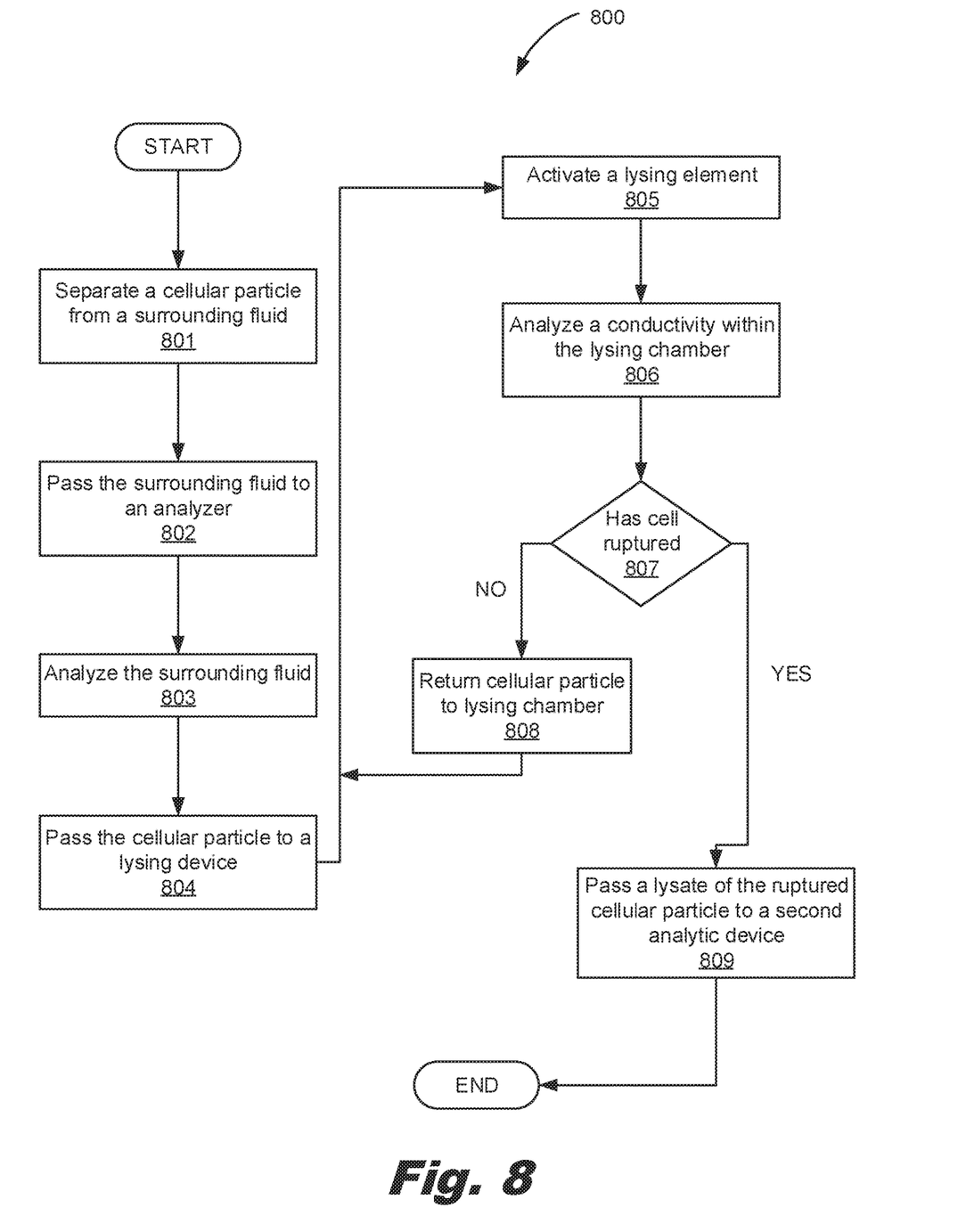
FIG. 8 is a flowchart of a method for serial separation and lysis in a serial cellular analytic system, according to an example of the principles described herein.

FIG. 8 is a flowchart of a method (800) for serial separation and lysis in a cellular analytic system (FIG. 1, 100), according to an example of the principles described herein. According to the method (800) a cellular particle is separated (block 801) from a surrounding fluid. The surrounding fluid is passed (block 802) to an analyzer (FIG. 1, 104) where it is analyzed (block 803). These operations may be performed as described above in connection with FIG. 4. The separated cellular particle is then passed (block 804) to a lysing device (FIG. 1, 108) as described above in connection with FIG. 4.

The lysing element (FIG. 3, 324) is activated (block 805) to carry out the desired lysing. Activating (block 805) the lysing element (FIG. 3, 324) may take many forms based on the type of lysing element (FIG. 3, 324) used. For example, it may include passing an electrical activation signal to the lysing element (FIG. 3, 324).

A conductivity within the lysing chamber (FIG. 3, 320) is then analyzed (block 806). It is then determined (block 807) whether the cellular particle membrane has ruptured. This may be done by analyzing measurements collected by the electrodes (FIG. 3, 322) as described above. If the cellular membrane has ruptured (block 807, determination YES), the lysate may be passed (block 809) to a second analytic device (FIG. 1, 102-2). By comparison, if the cellular particle membrane has not ruptured (block 807, determination NO), the cellular particle is returned (block 808) to the lysing chamber (FIG. 3, 320) where the lysing element (FIG. 3, 324) is again activated. Such a return (block 808) may include deactivating a main pump (FIG. 6, 630) and activating a return pump (FIG. 6, 634) to re-direct the cellular particle to the lysing chamber (FIG. 3, 320). That is, to ensure proper lysing, the un-lysed cellular particle is returned to the lysing chamber (FIG. 3, 320).

Figure 9:
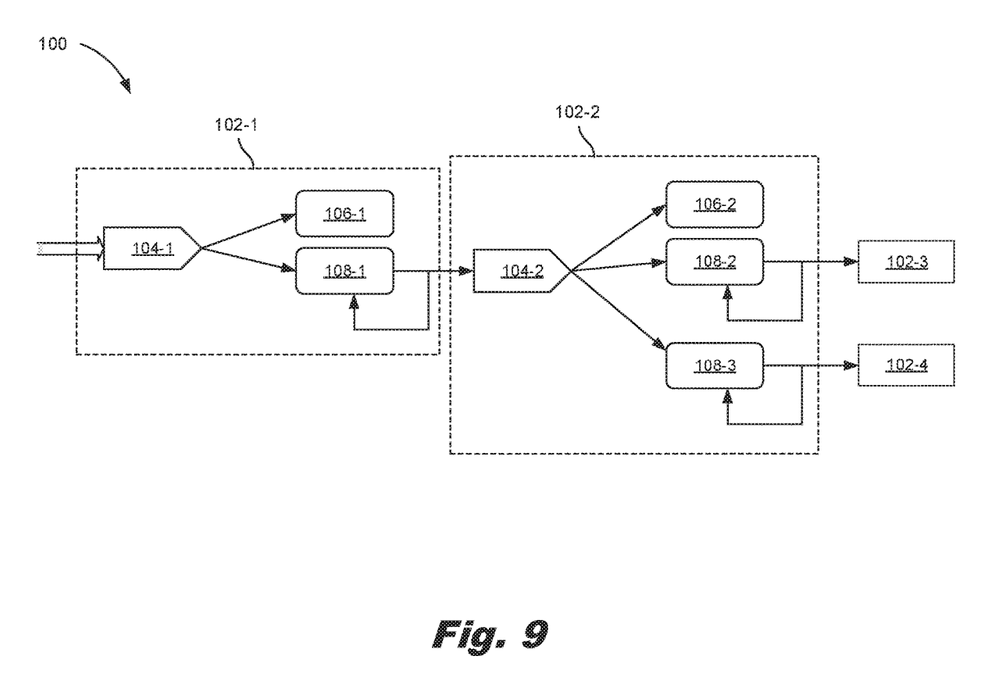
FIG. 9 is a diagram of a serial cellular analytic system, according to an example of the principles described herein.

FIG. 9 is a diagram of a serial cellular analytic system (100), according to an example of the principles described herein. In this example, the cellular analytic system (100) includes a first analytic device with its associated separator (104-1), analyzer (106-1), and lysing device (108-1). The cellular analytic system (100) also includes the second analytic device (102-2) with its associated separator (104-2) and analyzer (106-2).

However, in this example, rather than having just the second lysing device (108-2), the second analytic device (102-2) includes a third lysing device (108-3). For example, in this case, the second separator (104-2) separates multiple organelles, for example nuclei and mitochondria from the cytoplasmic fluid. The cytoplasmic fluid passes to the second analyzer (106-2), one organelle (e.g., the nuclei) passes through one outlet (FIG. 2, 218) of the separator (104-2) to the second monitored lysing device (108-2) and another organelle (e.g., the mitochondria) passes through another outlet of the separator (104-2) to a third monitored lysing device (108-3). In this example, the second monitored lysing device (108-2) ruptures a membrane of the nuclei and passes a nucleic fluid to a third analytic device (102-3) and the third monitored lysing device (108-3) ruptures a membrane of the mitochondria and passes a mitochondrial fluid to a fourth analytic device (102-4). That is, each lysing device (108) in a particular analytic device (102) may pass fluid onto a downstream analytic device (102), which downstream analytic device (102) may include its own separator (104), analyzer (106), and/or lysing device (108). For example, the fourth analytic device (102-4) may include a separator (104) that separates bacteria, parasites, and/or viral particles from a mitochondrial fluid. Thus as provided herein, the cellular analytic system (100) can accommodate a wide variety of operations, and an expandable tree of fluid analytic devices (102) to carry out an innumerable combinations of analytic and separating operations.

In summary, using such a cellular analytic system 1) automates the sequential analysis of different fluids within a sample; 2) enlarges the information collectable from a sample; 3) avoids contamination of fluid samples; and 4) reduces the number of samples used in multi-fluid analysis. However, the devices disclosed herein may address other matters and deficiencies in a number of technical areas.

What is claimed is:

1. A cellular analytic system, comprising:
   a series of analytic devices, each analytic device comprising:
      a separator to separate a cellular particle from a surrounding fluid;
      an analyzer coupled to a first outlet of the separator to analyze the surrounding fluid; and
      at least one lysing device coupled to at least a second outlet of the separator to rupture a membrane of the cellular particle, wherein an outlet of a lysing device is fluidly coupled to a separator of a downstream analytic device.

2. The system of claim 1, wherein the separator comprises a dielectrophoresis separator.

3. The system of claim 1, wherein the at least one lysing device comprises:
   a lysing chamber to receive the cellular particle;
   at least one lysing element to rupture a cellular particle membrane; and
   at least one pair of electrodes disposed in the lysing chamber to detect a level of conductivity in the lysing chamber.

4. The system of claim 3, wherein the system further comprises a controller to determine when the cellular particle membrane has ruptured based on detected levels of conductivity within the lysing chamber.

5. The system of claim 4, wherein the at least one lysing device further comprises a return pump to re-direct the cellular particle to the lysing chamber when the cellular particle membrane is not sufficiently lysed.

6. The system of claim 5, wherein the return pump re-directs the cellular particle to the lysing chamber through at least one of:

an outlet of the lysing chamber; and
a return channel.

7. The system of claim 1, wherein each analytic device is a microfluidic device.

8. The system of claim 1, wherein at least one analytic device comprises multiple lysing devices, each lysing device being coupled to a different outlet of the separator.

9. The system of claim 1, further comprising a pump disposed in an inlet of the separator to drive a sample through the separator.

10. The system of claim 1, further comprising a pump disposed in at least one outlet to draw a sample through the separator.

11. A method comprising:
   in a first analytic device:
      separating a cellular particle from a surrounding fluid;
      passing the surrounding fluid to an analyzer;
      analyzing the surrounding fluid;
      passing the cellular particle to a lysing chamber;
      rupturing a membrane of the cellular particle; and
   passing a lysate of the ruptured cellular particle to a second analytic device.

12. The method of claim 11, further comprising:
   measuring a conductivity within the lysing chamber; and
   analyzing the conductivity within the lysing chamber to determine that the cellular particle membrane has ruptured; and
   when the cellular particle is un-lysed, re-direct the cellular particle to the lysing chamber.

13. A cellular analytic system, comprising:
   a first analytic device comprising:
      a first separator to separate a cell from an extracellular fluid;
      a first analyzer coupled to a first outlet of the first separator to analyze the extracellular fluid; and
      a first monitored lysing device coupled to a second outlet of the first separator to rupture a membrane of the cell; and
   a second analytic device comprising:
      a second separator to separate organelles in the lysate of the cell from a cytoplasmic fluid;
      a second analyzer coupled to a first outlet of the second separator to analyze the cytoplasmic fluid; and
      a second monitored lysing device coupled to a second outlet of the second separator to rupture a membrane of a first organelle.

14. The system of claim 13, further comprising a third monitored lysing device coupled to a third outlet of the second separator to rupture a membrane of a second organelle.

15. The system of claim 14, wherein:
   the second separator separates nuclei and mitochondria in the lysate from the cytoplasmic fluid;
   the second monitored lysing device ruptures a membrane of the nuclei and passes a nucleic fluid to a third analytic device; and
   the third monitored lysing device ruptures a membrane of the mitochondria and passes a mitochondrial fluid to a fourth analytic device.

* * * * *